United States Patent [19]

Rabloczky et al.

[11] Patent Number: 4,785,104
[45] Date of Patent: Nov. 15, 1988

[54] 3-(HYDROXYMETHYL)-ISOQUINOLINE DERIVATIVES

[75] Inventors: György Rabloczky; Jenö Körösi; Tibor Láng; István Ling; Tamás Hámori; Mária Kuhár née Kürthy; István Elekes; Péter Botka; András Varró ; Sándor Elek; Judit Sárossy née Kincsessy; Gábor Zólyomi; Zsuzsanna Láng née Rihmer; Imre Moravcsik, all of Budapest, Hungary

[73] Assignee: EGIS Gyogyszergyar, Budapest, Hungary

[21] Appl. No.: 51,767

[22] Filed: May 20, 1987

[30] Foreign Application Priority Data

May 21, 1986 [HU] Hungary ............................ 2141/86

[51] Int. Cl.[4] .......................................... C07D 217/16
[52] U.S. Cl. ...................................... 546/144; 546/90
[58] Field of Search .................................. 546/144, 90

[56] References Cited

FOREIGN PATENT DOCUMENTS 2246307 2/1973 Fed. Rep. of Germany .

OTHER PUBLICATIONS

Valette, "Chemical Abstracts", vol. 79, 1973, Col. 5277m.
Lucas, *Organic Chemistry*, 2nd Ed., 1953, Amer. Book. Co., N.Y., pp. 213-227.
J. Chem. Soc., 1951, pp. 1951-1949.
Helv. Chim. Acta 31, 1978 (1948).
J. Am. Chem. Soc. 72, 1118 (1950).

*Primary Examiner*—Richard L. Raymond
*Assistant Examiner*—James H. Turnipseed
*Attorney, Agent, or Firm*—Keil & Weinkauf

[57] ABSTRACT

This invention relates to new 3-(hydroxymethyl)-isoquinoline derivatives of the general formula (I), their acid addition salts, and to a process for the preparation thereof, furthermore to pharmaceutical compositions containing the same,

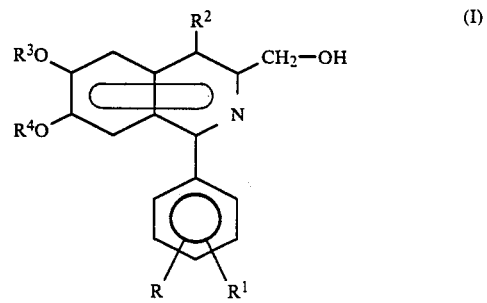

wherein
R and $R^1$ are identical or different and stand for a hydrogen or halogen atom, a nitro or a $C_{1-4}$ alkoxy group,
$R^2$ stands for a hydrogen atom or a $C_{1-4}$ alkyl group,
$R^3$ and $R^4$ are identical or different and stand for a hydrogen atom or a $C_{1-4}$ alkyl group, or $R^3$ and $R^4$ combined denote a methylene group,
with the proviso that when R stands for 3-methoxy, $R^1$ for 4-methoxy, $R^3$ and $R^4$ are identical and represent methyl or ethyl groups, $R^2$ is other than hydrogen atom.

The compounds of the general formula (I) exert valuable positive inotropic (cardiotonic) potency, they are capable to increase the myocardiac contractile force (heart performance in cardiac insufficiency), thus they can be applied in the therapy of chronic heart failure and coronary ailments.

2 Claims, No Drawings

3-(HYDROXYMETHYL)-ISOQUINOLINE DERIVATIVES

This invention relates to new 3-(hydroxymethyl)-isoquinoline derivatives of the general formula (I), their acid addition salts, and to a process for the preparation thereof, furthermore to pharmaceutical compositions containing the same,

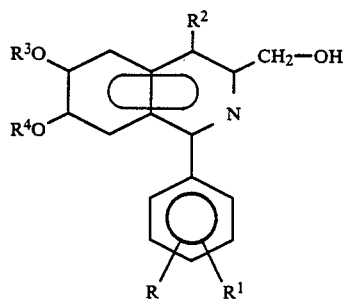
(I)

wherein

R and $R^1$ are identical or different and stand for a hydrogen or halogen atom, a nitro or a $C_{1-4}$ alkoxy group, $R^2$ stands for a hydrogen atom or a $C_{1-4}$ alkyl group, $R^3$ and $R^4$ are identical or different and stand for a hydrogen atom or a $C_{1-4}$ alkyl group, or $R^3$ and $R^4$ combined denote a methylene group, with the proviso that when R stands for 3-methoxy, $R^1$ for 4-methoxy, $R^3$ and $R^4$ are identical and represent methyl or ethyl groups, $R^2$ is other than hydrogen atom.

In the foregoing definitions the term "halogen atom" refers to fluorine, chlorine or bromine, the term "$C_{1-4}$ alkyl" covers straight-chained or branched, saturated aliphatic hydrocarbyl groups of one to four carbon atom(s) (e. g. methyl, ethyl, n-propyl, isopropyl, etc.). The term "$C_{1-4}$ alkoxy" refers to straight-chained or branched alkoxy groups containing one to four carbon atom(s) (e. g. methoxy, ethoxy, n-propoxy, isopropoxy, etc.).

Preferred representatives of the compounds having the general formula (I) are those described in the Examples.

Particularly preferred representatives of the compounds according to the invention are the following derivatives:

1-(3-chlorophenyl)-3-(hydroxymethyl)-6,7-dimethoxy-isoquinoline, 1-(3-nitrophenyl)-3-(hydroxymethyl)-6,7-dimethoxy-isoquinoline, 1-(3,4-dichlorophenyl)-3-(hydroxymethyl)-6,7-dimethoxy-isoquinoline, 1-(4-nitrophenyl)-3-(hydroxymethyl)-6,7-dimethoxy-isoquinoline, 1-(3,4-dimethoxyphenyl)-3-(hydroxymethyl)-4-ethyl-6,7-dimethoxy-isoquinoline, and the pharmaceutically acceptable acid addition salts thereof.

The compounds of the general formula (I) are new, except for two compounds (German patent specification No. 2,246,307), and exert a valuable positive inotropic (cardiotonic) effect not described in the literature. The hydrochloric and methanesulfonic acid salts of the known compounds exert spasmolytic activity which is lower than that of papaverine (German patent specification No. 2,246,307).

The process for the preparation of the compounds of the general formula (I) is also new.

The O-acyl derivatives of the general formula (III) prepared in the process of the invention are also new.

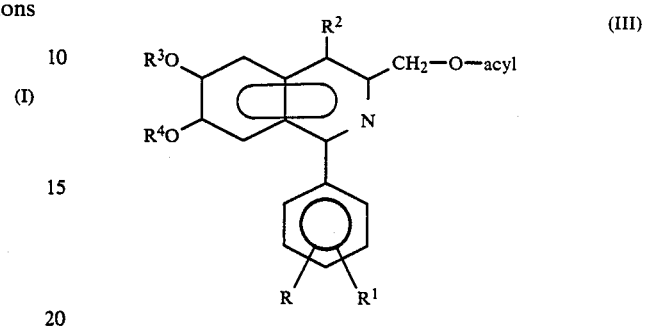
(III)

The 3-(hydroxymethyl)-isoquinolines can be prepared by the following methods described in the literature:

1. The ether cleavage in the 1-aryl-3-phenoxymethyl-3,4-dihydro-isoquinolines is peformed in the presence of air by refluxing with a 48% aqueous solution of hydrogen bromide (J. Ind. Chem. Soc. 38, 216 (1961)).

2. 3-Methyl-isoquinoline is first oxidized at 250° C. with selenium dioxide to isoquinoline-3-aldehyde which is subsequently reduced in the presence of potassium hydroxide with 40% formaline to 3-(hydroxymethyl)-isoquinoline (J. Chem. Soc. 1951, 1145).

3. 3-Methyl-isoquinoline is transformed by N-bromosuccinimide into 3-(bromomethyl)-isoquinoline which is converted with silver acetate to 3-(acetoxymethyl)-isoquinoline. The resulting ester is saponified in aqueous methanol by potassium hydroxide (Helv. Chim. Acta 31, 1978 (1948)).

4. 1-(3,4-Dimethoxyphenyl)-3-(methoxycarbonyl)-6,7-dimethoxy(diethoxy)-3,4-dihydro-isoquinoline is dehydrogenated with sulfur at 150° C., then the ester group in position 3 is reduced either by lithium-aluminium-hydride or alkali-borohydride (German patent specification No. 2,246,307).

It has been found that the 3-(hydroxymethyl)-isoquinolines of the general formula (I) can be prepared directly by the hydrolysis of novel 3-(acyloxymethyl)-isoquinoline derivatives of the general formula (III), prepared from isoquinoline N-oxides of the general formula (II) with carbonic acid anhydride.

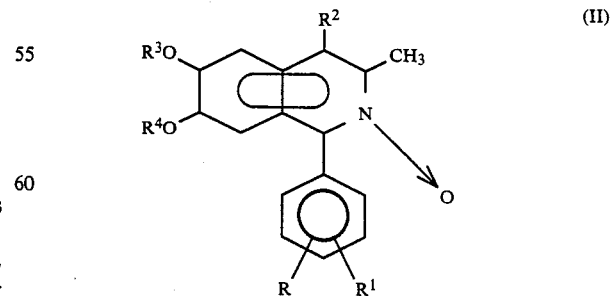
(II)

The advantages of the process of the invention compared to those described in the literature are the following:

It is not necessary to use 3-methyl-3,4-dihydroisoquinoline
or 3-methyl-isoquinoline derivatives as starting materials which can be prepared only at rather low yields, and where dehydrogenation can be performed only at high temperatures (with sulfur at 150° C.), or where oxidation with selenium dioxide is expensive (at 250° C.).

It is not necessary to peform bromination with the expensive and high molecular weight N-bromo-succinimide, nor to carry out reduction with complex metal hydride in anhydrous solvents.

The starting materials of the general formula (II) can be prepared with good yields, and
the compounds of the general formula (I) can be prepared from them in simple reactions, using inexpensive auxiliary materials.

According to the present invention there is provided a process for the preparation of the compounds of the general formula (I), wherein R, $R^1$, $R^2$, $R^3$ and $R^4$ have the same meaning as above, and their acid addition salts consisting of hydrolyzing a 3-(acyloxyemthyl)-isoquinoline derivative of the general formula (III), wherein R, $R^1$, $R^2$ have the same meaning as above, $R^3$ and $R^4$ have the same meaning as above but can represent also an acyl group, and the resulting acid addition salt of the compound of the general formula (I) is optionally converted to the free base or to another acid addition salt.

According to a preferred embodiment of the process of the invention the compounds of the general formula (III) are hydrolyzed by refluxing in dilute aqueous hydrochloric acid, resulting in the hydrochlorides of the compounds of the general formula (I) poorly soluble in water which can be isolated directly. If the hydrochloride of a compound of the general formula (I) is readily soluble in water, preferably it should be first transformed into the free base be treatment with an alkali.

The base can be isolated directly from the reaction mixture preferably by neutralizing the cooled reaction mixture with a dilute aqueous inorganic base, such as sodium hydroxide solution, or with an organic base, such as triethylamine. The crystals formed are filtered and, if desired, purified by recrystallization. The resulting base can be optionally converted into another acid addition salt with an aqueous acid solution.

According to a further preferred embodiment of the present invention the compounds of the general formula (III) are hydrolized by refluxing with a dilute aqueous base, preferably sodium hydroxide solution, the product is isolated and, if desired, purified by recrystallization.

In the above reaction the compounds of the general formula (I) are obtained as bases. The salts thereof are preferably formed by dissolving or suspending the base in an appropriate solvent, e. g. methanol, ethanol, isopropanol or water, and adding to the solution a suitable acid, e. g. hydrogen chloride, hydrogen bromide, phosphoric acid, sulfuric acid, acetic acid, citric acid, succinic acid, maleic acid, fumaric acid, or a solution thereof in an appropriate solvent. The salts are separated by filtration or evaporation of the solvent, and if desired, converted again into other acid addition salts.

The 3-(acyloxymethyl)-isoquinoline derivatives of the general formula (III) applied as starting compounds in the process of the invention are also new. According to a preferred embodiment of the process of the invention they can be prepared by refluxing 3-methyl-isoquinoline N-oxides of the general formula (II), wherein R, $R^1$, $R^2$, $R^3$ and $R^4$ have the same meaning as above, with a carboxylic acid anhydride, preferably with acetic anhydride or propionic anhydride, for one to five hours. The resulting 3-(acyloxymethyl)-isoquinoline derivative of the general formula (III) is isolated after concentrating the reaction mixture at reduced pressure and refrigerating the concentrate or by direct crystallization, if desired, by repeated crystallizations. Ethanol is preferably used as recrystallizing solvent. Under the acylating conditions applied the isoquinoline skeleton may become acylated in both positions 6 and 7, consequently in the intermediates of the general formula (III) $R^3$ and $R^4$ can represent preferably an acetyl or propionyl group. During hydrolysis these acyl groups are also cleaved. In the above process the intermediates of the general formula (III) can be prepared with very good yields (70 to 94%) and are converted also with very high yields into the 3-(hydroxymethyl)-isoquinolines of the general formula (I).

The compounds of the general formula (II) are partly known and partly new compounds, and can be prepared according to the following literature processes from 2-aroyl-phenylacetone derivatives in a reaction with hydroxylamine: E. Ochai: "Aromatic Amine Oxides", Elsevier Publishing Co., Amsterdam, London, New York, 1967, pp. 19–66; only the reaction of homophthalaldehyde with hydroxylamine is described: [J. Am. Chem. Soc. 72, 1118 (1950); J. Org. Chem. 19, 1533 (1954)].

The new compounds of the general formula (I) of the invention posses valuable positive inotropic (cardiotonic) effects which were confirmed in in vivo experiments according to the following methods. The known compounds isoproterenol (N-isopropyl-noradrenaline hydrochloride) and amrinone (inocor: 5-amino-3,4'-dipyridyl-6[1H]-one) served as controls.

METHODS (A) "Strain-gauge" method in anaesthetized, openchest cats

Male and female cats, weighing 2 to 5 kg, were anaesthetized with a 1:5 mixture of chloralose-urethane and artificial respiration was arranged through a tracheal cannule with a Harvard 665 A respirator. After opening the chest and the pericardium a strain-gauge was sutured onto the epicardial surface of the left ventricle according to the method of Walton and Brodie [J. Pharmacol. Exp. Ther. 90, 26 (1947)], and the myocardial contractile force (MCF) was measured. The test compounds were administered through venous and duodenal cannules, i.v. and i.d., resp. Arterial blood pressure was continuously monitored by an electromanometer through a catheter inserted in the femoral artery and joined to a Statham P 23 DB transducer. The heart rate was continuously recorded by a pulsotachometer.

Fifteen minutes before each experiment the reactivity of the cat heart was controlled by applying i.v. 0.2 µg/kg of isoproterenol. Then the test compound was administered i.v. in a dose of 5 mg/kg. In these experiments isoproterenol served not as the usual reference compound. It was used partly to control the responsiveness of the test system and partly to assess the potency of the test compounds. The relative potency of the test compounds was expressed by comparing the effect induced in MCF by 5 mg/kg i.v. of the test compound to that of 0.2 µg/kg i.v. of isoproterenol in the same cat. The values obtained are good indicators of the positive inotropic effect of a compound as the individual sensitivity of the animals can be excluded in this way. The results are presented in Table 1.

The compound of Example 1 proved to be a potent agent also at i.d. administration. A 5 mg/kg dose increased MCF by 75% (Table 1).

equiactive or more potent than amrinone used as reference compound. The duration of the effect is also significant compared to isoproterenol where it lasted for 4 to 5 min. while after the administration of the compounds listed in Tables 1 and 2 this effect lasted for up to 110 min.

TABLE 1

Positive inotropic effect in anaesthetized, open-chest cats

| Compound Example No | Route of administration | Dose mg/kg | MCF % | Relative potency compared to iso-proterenol | Duration of effect min. | HR min.$^{-1}$ | $P_A$ Hgmm |
|---|---|---|---|---|---|---|---|
| 1 | i.v. | 5 | +50 | 2.2 | 60 | +20 | −25 |
|  | i.d. | 5 | +75 |  | 40 | +12 | −5 |
| 2 | i.v. | 5 | +60.9 | 1.14 | 110 | +45 | −63.3 |
| 9 | i.v. | 5 | +45.45 | 0.89 | 34 | −45 | −45 |
| 17 | i.v. | 5 | +36.25 | 0.79 | 26 | 0 | −15 |
| 18 | i.v. | 5 |  | 1 | 11 | +15 | −46.6 |
| Isoproterenol | i.v. | 0.2 µg/kg |  | 1 | 4.76 | +44.5 | −33.05 |
| Amrinone | i.v. | 5 |  | 1.5 | >60 | +40 | −28.3 |

MCF: increase in myocardial contractile force
HR: change in heart rate
$P_A$: decrease in systemic arterial blood pressure (B) Testing in anaesthetized, open-chest dogs The myocardial and coronary vascular effects (coronary flow effects) of the compound of Example 1 of the invention were tested in mongrel dogs of both sexes anaesthetized with 30 mg/kg of pentobarbital sodium. Applying the procedure described under A) the changes in coronary flow were measured with Narcomatic RT-500, the systemic arterial blood pressure, heart rate and MCF were monitored accordingly. The results are presented in Table 2.

TABLE 2

Positive inotropic effect in anaesthetized open-chest dogs

| Compound Example No. | Dose mg/kg | MCF % | Duration of effect min. | HR min.$^{-1}$ | $P_A$ Hgmm | Flow % |
|---|---|---|---|---|---|---|
| 1 | 0.5 | +42 | 40* | +23 | −16 | +27 |
|  | 1.0 | +57 | 18 | +40 | −23 | +58 |
|  | 2.0 | +70 | 70 | +25 | −33 | +112 |
|  | 4.0 | +61 | 58 | +36 | −45 | +151 |
| Amrinone | 2.0 | +64 | 33 | +25 | −28 | +77 |

MCF: increase of myocardial contractile force
HR: increase of heart rate
$P_A$: decrease of systemic arterial blood pressure
Flow: change of coronary blood flow (ml/min.)
*unsignificant Tables 1 and 2 demonstrate that as regards the MCF increasing effect the compounds of the invention are In a separate part of the experiments coronary flow was temporarily stopped (40 min.) by occlusion of the left anterior descendent coronary artery and thereafter cardiac effects were tested again in the acutely ischemized myocard. Table 3 demonstrates the effects of the compound of Example 1 after acute ischemia induced by transient coronary occlusion. Positive inotropic effects were somewhat weaker than in the intact myocard but those induced by the higher dose remained significant. The compound caused positive inotropic effect even after i.d. administration: the 1 mg/kg dose induced about 20% while 5 mg/kg dose about 50% increase of MCF.

(C) Investigations in anaesthetized dogs with partly infarcted myocard

These animals had been previously operated to induce acute myocardial infarct by ligating one segment of the left anterior descendent coronary artery. Thereafter, if they survived for at least six weeks, they were anaesthetized again and the above pharmacological testing was performed. At the infarcted area (diameter about 4 cm) the ventricular wall became rather thin and was transformed into an inactive connective tissue-like material.

TABLE 3

Positive inotropic effect in anaesthetized open-chest dogs of acute myocardial ischemia

| Compound Example No. | Dose mg/kg | MCF % | Duration of effect min. | HR min.$^{-1}$ | $P_S$ Hgmm | $P_D$ Hgmm | Flow % |
|---|---|---|---|---|---|---|---|
| 1 | 0.5 | +23.9 | 25.66 | +16.0* | −13.0** | −21.0* | +34.2* |
|  |  | ±8.4 | ±12.3 | ±4.0 | ±2.0 | ±4.9 | ±6.7 |
|  | 1.0 | +30.9* | 21.3* | +35.8* | −23.3* | −22.5* | +48.7* |
|  |  | ±6.4 | ±4.0 | ±10.4 | ±4.4 | ±3.8 | ±16.1 |
| Amrinon | 0.5 | +27.9 | 12.6 | +14.0 | −8.0 | −14.0 | +25.9 |
|  |  | ±13.0 | ±4.2 | ±2.9 | ±3.4 | ±2.4 | ±7.9 |
|  | 1.0 | +39.7* | +11.8* | +16.0 | −13.0 | −17.0 | +44.5** |
|  |  | ±10.0 | ±3.5 | ±2.4 | ±3.7 | ±2.0 | ±7.8 |

*p < 0.05
**p < 0.01
MCF = increase of myocardial contractile force
HR = increase of heart rate
$P_S$ = decrease of systolic blood pressure
$P_D$ = decrease of diastolic blood pressure
Flow = increase of coronary blood flow The data of Table 4 demonstrate that the compound of Example 1 was able to evoke significant increase of MCF in dogs with infarcted myocard, too.

TABLE 4

Positive inotropic effect in anaesthetized, open-chest dogs with infarcted myocard

| Compound Example No. | Dose mg/kg | MCF % | Duration of effect min. | HR min.$^{-1}$ | $P_S$ Hgmm | $P_D$ Hgmm | Flow % |
|---|---|---|---|---|---|---|---|
| 1 | 0.5 | +56.7* ±16.9 | 33 | +31.3* ±5.5 | −15.0* ±2.9 | −42.5* ±9.5 | +66.6* ±6.9 |
|   | 1.0 | +91.2** ±15.5 | 45 | +71.2** ±3.1 | −37.5 ±13.7 | −55.0** ±5.0 | +74.3* ±9.7 |

*p < 0.05
**p < 0.01
MCF = increase in myocardial contractile force
HR = increase of heart rate
$P_S$ = decrease of systolic blood pressure
$P_D$ = decrease of diastolic blood pressure
Flow = increase of coronary blood flow (D) Investigations in intact conscious chronically cannulized cats These animals were used according to either the method of Rabloczky and Mader ("Measurement of Systemic and Pulmonary Arterial Pressure in Conscious Animals", lecture at the Congress of the International Union of Pharmacologists, Budapest, 1980) or a modification thereof. Systemic arterial cannule was inserted into the ventricle for intraventricular pressure measurement and determination of dp/dt, indicating the response of the MCP. The compound of Example 1 was administered orally in doses of 1 and 2 mg/kg. The compound induced a persistent (lasting for 45 min.) 30 to 50 percent increase of MCF while it did not significantly alter either the systemic blood pressure or heart rate.

The above-mentioned experiments were carried out on conscious cats which had a partly infarcted myocard, too. These animals had been previously operated to induce acute myocardial infarct by ligating one segment of the left anterior descendent coronary artery. After four weeks the cats had been cannulized. The data of Table 5 demonstrate that the compound of Example 1 induced a significant increase of MCF in conscious cats with an infarcted myocard which was even more significant than that found in cats with intact myocard.

TABLE 5

Positive inotropic effect of the compound of Example 1 in conscious cats with infarcted and intact myocard (1 mg/kg p.o.)

| | Time min. | $P_S$ Hgmm | $P_D$ Hgmm | HR min.$^{-1}$ | MCF % |
|---|---|---|---|---|---|
| Conscious cat with infarcted myocard | Base | 118 ± 16 | 76 ± 12 | 170 ± 5.7 | 100 |
| | 15 | 106 ± 23 | 70 ± 17 | 165 ± 9.6 | 113.7 ± 4.6 |
| | 30 | 108 ± 16 | 88 ± 16 | 182 ± 13.1 | 140.7 ± 11.6* |
| | 45 | 111 ± 12 | 75 ± 7 | 170 ± 10.0 | 138.7 ± 7.4* |
| | 60 | 115 ± 7 | 76 ± 6 | 182 ± 10.3 | 152.5 ± 24.0 |
| | 75 | 115 ± 10 | 73 ± 8 | 175 ± 11 | 141.0 ± 19.8 |
| | 90 | 118 ± 6 | 78 ± 6 | 175 ± 12.5 | 123.5 ± 14.6 |
| Conscious cat with intact myocard | Base | 124 ± 3 | 84 ± 2 | 170 ± 9.6 | 100 |
| | 15 | 120 ± 3 | 80 ± 2 | 183 ± 15.2 | 117 ± 7 |
| | 30 | 121 ± 4 | 80 ± 2 | 195 ± 15.6 | 134 ± 13* |
| | 45 | 128 ± 4 | 82 ± 2 | 190 ± 14.2 | 132 ± 9* |
| | 60 | 131 ± 3 | 88 ± 3 | 188 ± 15.7 | 137 ± 11* |
| | 75 | 127 ± 4 | 85 ± 3 | 190 ± 15.1 | 124 ± 4* |
| | 90 | 122 ± 3 | 81 ± 2 | 176 ± 11.1 | 105 ± 3 |

*p < 0.05
MCF = myocardial contractile force
HR = heart rate
$P_S$ = systolic blood pressure
$P_D$ = diastolic blood pressure In the anaesthetized cat the compound of Example 1 proved to be more potent than amrinone, its i.d. potency surpassed that of i.v. activity which indicates good oral absorptivity. In the biochemical tests the compound of Example 1 inhibited phosphodiesterase activity. This effect alone could be held responsible for the positive inotropic action, but it was accompanied by a coronary vasodilator activity promoting the main effect of the agent. In the chronic phase of myocardiac infarct of dogs the cardiac tissue was more sensitive toward the positive inotropic effect of the compound of Example 1 than in the intact one.

Unlike the other compounds, the compound of Example 9 does not increase but decreases the heart rate (bradycardia).

According to a further feature of the present invention there are provided new pharmaceutical compositions containing as active ingredient at least one compound of the general formula (I) or a pharmaceutically acceptable acid addition salt thereof, together with one or more pharmaceutical carrier(s), diluent(s) and/or additive(s). The pharmaceutical compositions may contain also other biologically active substances, particularly other cardiotonic agents.

The pharmaceutical compositions can be formulated in solid (such as tablets, coated tablets, capsules, etc.) or in liquid forms (such as solutions, suspensions, emulsions, etc.). The carriers may be such as generally used in pharmacy (e.g. starch, magnesium stearate, magnesium carbonate, talc, stearine, gelatine, lactose, cellulose, calcium carbonate, polyvinyl pyrrolidone, water, polyalkylene glycol, etc.). The compositions may also contain suitable additives (e.g. suspending, emulsifying, stabilizing agents, buffers, etc.) and therapeutically valuable further agents.

The compositions can be presented in the form of orally or parenterally administerable further agents.

The pharmaceutical compositions can be prepared by methods generally applied in the pharmaceutical industry.

The daily dose of the new compounds according to the inventions is about 2 to 200 mg, the accurate dose being dependent on the body weight, age and general health condition of the patient.

The compounds of the invention were identified beyond elementary analysis by IR and $^1$H NMR spectroscopy as well as mass spectrometry.

The invention is illustrated in detail by the following non-limiting Examples.

EXAMPLE 1

1-(3-Chlorophenyl)-3-(hydroxymethyl)-6,7-dimethoxy-isoquinoline hydrochloride 15.67 g (0.042 M) of 1-(3-chlorophenyl)-3-(acetoxymethyl)-6,7-dimethoxy-isoquinoline (compound of Example 21) are refluxed in 160 ml of an aqueous 5% solution of hydrochloric acid for one hour. The crystals of the end-product are rapidly beginning to form from the initially clear solution. After ice-cooling the reaction mixture is filtered, the product is washed with 3×10 ml of water and dried at 90° to 100° C., giving 15.21 g of a crude product, m.p. 210° to 214° C. The crude product is purified by refluxing in 180 ml of 99.5% ethanol, the suspension is cooled and kept at +5° C. for 10 hours, then it is filtered, washed with 3×5 ml of ethanol and dried. Yield 12.67 g (82.4%), m. p. 219° to 221° C. d.

The hydrochloride salts of the compounds prepared according to the procedure described in Example 1 are presented in Table 6.

TABLE 6

| Example No. | R | R$^1$ | R$^2$ | R$^3$ | R$^4$ | Yield % | M.p. (°C.) (recrystallizing solvent) |
| --- | --- | --- | --- | --- | --- | --- | --- |
| 2 | 3-NO$_2$ | H | H | Me | Me | 92.6 | 228–230 d. (digerated in ethanol) |
| 3 | H | H | H | Me | Me | 89.4 | 230–232 d. (anhydrous ethanol) |
| 4 | 3-NO$_2$ | 4-Cl | H | Me | Me | 84.4 | 222–224 d. (digerated in ethanol) |
| 5 | 2-Cl | 4-NO$_2$ | H | Me | Me | 64.0 | 221–223 d. (digerated in ethanol) |
| 6 | 3-Cl | H | H | H | Me | 49.5 | 217–219 d. (EtOH/EtOAc) |
| 7 | 4-NO$_2$ | H | H | —CH$_2$— | | 61.3 | 224–226 d. (digerated in ethanol) |
| 8 | 3-Cl | H | H | Et | Et | 69.0 | 219–221 d. (anhydrous ethanol) |
| 9 | 3-Cl | 4-Cl | H | Me | Me | 87.3 | 227–229 d. (digerated in ethanol) |
| 10 | H | H | H | Et | Et | 83.7 | 215–217 d. (anhydrous ethanol) |
| 11 | 3-Cl | 4-Cl | H | Et | Et | 87.5 | 232–234 d. (digerated in ethanol) |
| 12 | 4-Br | H | H | Et | Et | 69.4 | 216–218 d. (anhydrous ethanol) |
| 13 | H | H | H | —CH$_2$— | | 67.7 | 190–192 d. (isopropanol) |
| 14 | 4-Br | H | H | —CH$_2$— | | 57.8 | 219–221 d. (anhydrous ethanol) |
| 15 | 3-OMe | 4-OMe | H | —CH$_2$— | | 50.7 | 247–249 d. (dimethylformamide) |

EXAMPLE 16

1-(3-Chlorophenyl)-3-(hydroxymethyl)-6,7-dimethoxy-isoquinoline

A mixture of 24.77 g (0.0676 M) of 1-(3-chlorophenyl)-3-(hydroxymethyl)-6,7-dimethoxy-isoquinoline hydrochloride (compound of Example 1), 150 ml of chloroform and 10.1 g (13.9 ml, 0.1 M) of triethylamine is refluxed for 15 minutes. After cooling the solution is extracted with 3×50 ml of water, the chloroform layer is dried over anhydrous sodium sulfate, evaporated, giving the aimed product in crystalline, base form. This base is purified by dissolving in 25 ml of hot 99.5% ethanol. After cooling the resulting crystalline mass is mixed with 25 ml of diethyl ether, cooled, filtered, washed with 3×5 ml of a mixture (1:1) of ethanol and ether, and subsequently dried at 60° to 80° C. Yield 16.73 g (75.1%), m.p. 118° to 120° C.

EXAMPLE 17

1-(4-Nitrophenyl)-3-(hydroxymethyl)-6,7-dimethoxy-isoquinoline 3.96 g (10.36 mM) of 1-(4-nitrophenyl)-3-(acetoxymethyl)-6,7-dimethoxy-isoquinoline (compound of Eaxmple 23) is hydrolized according to the procedure described in Example 1, and the resulting hydrochloride salt of the aimed product is filtered. The base is liberated from this salt by the procedure described in Example 16, giving 3.35 g (95%) of a crude product, m. p. 260° to 263° C. which is recrystallized from 15 ml of dimethylformamide. Yield 2.94 g (83.4%), m. p. 267° to 269° C.

EXAMPLE 18

1-(3,4-Dimethoxyphenyl)-3-(hydroxymethyl)-4-ethyl-6,7-dimethoxy-isoquinoline

A mixture of 394.0 g (0.926 M) of 1-(3,4-dimethoxyphenyl)-3-(acetoxymethyl)-4-ethyl-6,7-dimethoxy-isoquinoline (compound of Example 20) or 407.0 g (0.926 M) of 1-(3,4-dimethoxyphenyl)-3-propionyloxymethyl-4-ethyl-6,7-dimethoxy-isoquinoline (compound of Example 38) and 2.76 liters of 5% aqueous hydrochloric acid is refluxed for one hour. The reaction mixture is cooled, poured into 1.98 liters of an aqueous 10% solution of sodium hydroxide, cooled to 5° C., the crystals formed are filtered, washed with 4×300 ml of water and dried at 80° to 100° C., giving 365 to 375 g of a crude product, m. p. 160° to 163° C. This product is recrystallized from one liter of ethyl acetate. Yield 322.5 g (91.0%), m. p. 164° to 166° C.

Preparation of the hydrochloride salt 2.5 g of the above base, 80 ml of 99% ethanol and 3 ml of 20% hydrochloric acid are refluxed for 30 minutes, the solution is evaporated and the residue is recrystallized from 35 ml of 99% ethanol. Yield 2.43 g (88.7%), m. p. 204° to 206° C. d.

EXAMPLE 19

1-(3-Nitro-4-chlorophenyl)-3-(hydroxymethyl)-6,7-diethoxy-isoquinoline 4.98 g (0.0112 M) of 1-(3-nitro-4-chlorophenyl)-3-(acetoxymethyl)-6,7-diethoxy-isoquinoline is refluxed with 50 ml of a 10% aqueous sodium hydroxide solution for 5 hours. During the hydrolysis the product is precipitated . The suspension formed is cooled, filtered, washed with water to remove sodium hydroxide, and dried. The crude product (4.27 g) is purified by treating it with 45 ml of hot, anhydrous ethanol, the suspension is cooled with ice-water, filtered, washed with 3×5 ml of anhydrous ethanol and dried. Yield 3.94 g (87.4%), m. p. 187° to 188° C.

Preparation of the hydrochloride salt

The above base is refluxed with 60 ml of an aqueous 5% solution of hydrochloric acid, the suspension is cooled with ice-water, filtered, washed with 4×10 ml of distilled water and dried at 80° to 100° C. Yield 4.08 g (83%), m. p. 219° to 221° C b.

The new 3-(acyloxymethyl)-isoquinoline derivatives of the general formula (III), serving as starting materials in the process for the preparation of the acid addition salts of the compounds of the general formula (I) according to Examples 1 to 19, are synthesized according to the following Examples 20 to 37.

EXAMPLE 20

1-(3,4-Dimethoxyphenyl)-3-(acetoxymethyl)-4-ethyl-6,7-dimethoxy-isoquinoline 421.5 g (1.1 M) of 1-(3,4-dimethoxyphenyl-3-methyl-4-ethyl-6,7-dimethoxy-isoquinoline N-oxide and 1.1 liters of acetic anhydride are refluxed for 2.5 hours, then the solution is evaporated at reduced pressure. The residue is recrystallized first from 1.2 liters of 99% ethanol, then the resulting product (414.5 g, m. p. 115° to 120° C.) is repeatedly recrystallized from one liter of 99% ethanol. Yield 393.7 g (84.1%), m.p. 129° to 131° C.

The further compounds of the general formula (III) prepared according to the procedure described in Example 20 are presented in Table 7.

TABLE 7

| Example No. | R | $R^1$ | $R^2$ | $R^3$ | $R^4$ | Yield % | M.p. (°C.) (recrystallizing solvent) |
|---|---|---|---|---|---|---|---|
| 21 | 3-Cl | H | H | Me | Me | 70.4 | 94–96 (anhydrous ethanol) |
| 22 | 3-NO₂ | H | H | Me | Me | 72.4 | 168–170 (anhydrous ethanol) |
| 23 | 4-NO₂ | H | H | Me | Me | 91.0 | 202–204 (anhydrous ethanol) |
| 24 | H | H | H | Me | Me | 79.1 | 158–160 (anhydrous ethanol) |
| 25 | 3-NO₂ | 4-Cl | H | Me | Me | 85.0 | 179–181 (digerated in ethanol) |
| 26 | 3-Cl | 4-No₂ | H | Me | Me | 93.9 | 185–187 (digerated in ethanol) |
| 27 | 3-Cl | H | H | Ac | Me | 40.7 | 120–122 (ethanol) |
| 28 | 4-NO₂ | H | H | —CH₂— | | 86.7 | 192–194 (digerated in ethanol) |
| 29 | 3-Cl | H | H | Et | Et | 86.8 | 87–89 (anhydrous ethanol) |
| 30 | 3-Cl | 4-Cl | H | Me | Me | 82.2 | 144–146 (anhydrous ethanol) |
| 31 | H | H | H | Et | Et | 75.8 | 114–116 (anhydrous ethanol) |
| 32 | 3-Cl | 4-Cl | H | Et | Et | 88.0 | 154–156 (anhydrous ethanol) |
| 33 | 3-NO₂ | 4-Cl | H | Et | Et | 80.9 | 152–154 (digerated in ethanol) |
| 34 | 4-Br | H | H | Et | Et | 90.9 | 149–151 (anhydrous ethanol) |
| 35 | H | H | H | —CH₂— | | 81.3 | 117–119 (anhydrous ethanol) |
| 36 | 4-Br | H | H | —CH₂— | | 85.0 | 128–130 (anhydrous ethanol) |
| 37 | 3-OMe | 4-OMe | H | —CH₂— | | 82.5 | 230–231 d. (hydrochloride) |

EXAMPLE 38

1-(3,4-Dimethoxyphenyl)-3-(propionyloxymethyl)-4-ethyl-6,7-dimethoxy-isoquinoline 3.83 g (10 mM) of 1-(3,4-dimethoxyphenyl)-3-methyl-4-ethyl-6,7-dimethoxy-isoquinoline N-oxide is refluxed with 20 ml of propionic anhydride for 1.5 hours. The solution is evaporated at reduced pressure, the residue is suspended in 100 ml of water, filtered, washed with 3×15 ml of water, dried at reduced pressure at room temperature, recrystallized from 7 ml of 99.5% ethanol, filtered, washed with 3×8 ml of ethanol and dried at 80° to 90° C. Yield 2.70 g (61.5%), m.p. 125° to 127° C.

EXAMPLE 39

Preparation of tablets

| Composition (for 1000 tablets) | g |
|---|---|
| 1-(3-chlorophenyl)-3-(hydroxymethyl)-6,7-dimethoxy-isoquinoline hydrochloride | 10 |
| Lactose | 185 |
| Microcrystalline cellulose | 25 |
| Talc | 5 |
| Corn starch | 73 |
| Magnesium stearate | 2 |
| Total: | 300 |

The above ingredients are mixed, homogenized and compressed to tablets containing 10 mg of the active ingredient each.

EXAMPLE 40

Preparation of an injectable solution

| Composition (for 2 liters of solution) | |
|---|---|
| 1-(3-Chlorophenyl)-3-(hydroxymethyl)-6,7-dimethoxy-isoquinoline hydrochloride | 20 g |
| Sodium chloride | 20 g |
| Water for injection purposes q.s. ad | 2000 ml |

The solution is filled into ampoules containing 2 ml of the solution each.

What we claim is:

1. New 3-(hydroxymethyl)-isoquinoline derivatives of the general formula (I),

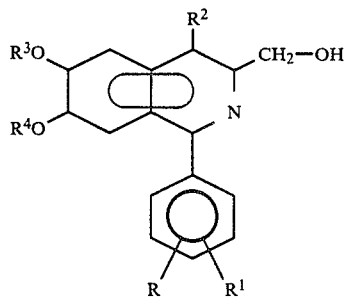

wherein

R and R¹ are identical or different and stand for a hydrogen or halogen atom, a nitro or a $C_{1-4}$ alkoxy group, R² stands for a hydrogen atom or a $C_{1-4}$ alkyl group, R³ and R⁴ are identical or different and stand for a hydrogen atom or a $C_{1-4}$ alkyl group, or combined denote a methylene group, with the proviso that if R stands for 3-methoxy, R¹ for 4-methoxy, R³ and R⁴ are identical and represent methyl or ethyl groups, R² is other than hydrogen atom, and pharmaceutically acceptable acid addition salts thereof.

2. A compound selected from the group consisting of 1-(3-chlorophenyl)-3-(hydroxymethyl)-6,7-dimethoxy-isoquinoline, 1-(3-nitrophenyl)-3-(hydroxymethyl)6,7-dimethoxy-isoquinoline, 1-(3,4-dichlorophenyl)-3-(hydroxymethyl)-6,7-dimethoxy-isoquinoline, 1-(4-nitrophenyl)-3-(hydroxymethyl)-6,7-dimethoxy-isoquinoline, 1-(3,4-dimethoxyphenyl)-3-(hydroxymethyl)-4-ethyl-6,7-dimethoxy-isoquinoline, and pharmaceutically acceptable acid addition salts thereof.

* * * * *